(12) United States Patent
Nordin et al.

(10) Patent No.: US 10,285,785 B2
(45) Date of Patent: May 14, 2019

(54) ABUTMENT FOR A DENTAL IMPLANT

(76) Inventors: Peter Nordin, Chernex (CH); Harald Nordin, Chernex (CH)

( * ) Notice: Subject to any disclaimer, the term of this patent is extended or adjusted under 35 U.S.C. 154(b) by 0 days.

(21) Appl. No.: 13/358,844

(22) Filed: Jan. 26, 2012

(65) Prior Publication Data

US 2012/0288825 A1  Nov. 15, 2012

(30) Foreign Application Priority Data

May 10, 2011 (EP) ..................... 11165565

(51) Int. Cl.
*A61C 8/00* (2006.01)

(52) U.S. Cl.
CPC ............ *A61C 8/005* (2013.01); *A61C 8/0069* (2013.01); *A61C 8/0074* (2013.01); *A61C 8/0012* (2013.01)

(58) Field of Classification Search
CPC ...... A61K 6/0044; A61K 6/08; A61K 6/0073; A61K 6/0005; A61K 6/0205; A61C 8/005; A61C 8/0012; A61C 8/0016; A61C 8/0018; A61C 8/0069; A61C 8/006; A61C 8/0054
USPC ....... 433/172–176, 224, 225, 201.1
See application file for complete search history.

(56) References Cited

U.S. PATENT DOCUMENTS

| | | | |
|---|---|---|---|
| 3,971,134 A | 7/1976 | Bokros | 32/10 A |
| 4,195,409 A | 4/1980 | Child | 433/175 |
| 4,252,525 A | 2/1981 | Child | 433/173 |
| 4,609,354 A | 9/1986 | Koch | 433/173 |
| 5,026,280 A | 6/1991 | Dürr et al. | 433/175 |
| 5,328,372 A * | 7/1994 | Reynaud et al. | 433/220 |
| 5,360,482 A * | 11/1994 | Belvedere | 118/404 |
| 5,453,007 A | 9/1995 | Wagher | 433/177 |
| 5,509,804 A | 4/1996 | Arzt | 433/169 |
| 5,584,693 A * | 12/1996 | Nishihara | 433/169 |
| 5,797,748 A * | 8/1998 | Reynaud | A61C 13/30 |
| | | | 433/220 |
| 5,816,816 A | 10/1998 | Scharf | 433/220 |
| 5,853,653 A | 12/1998 | Donato et al. | 264/625 |
| 5,861,445 A * | 1/1999 | Xu et al. | 523/116 |
| 5,890,904 A | 4/1999 | Reynaud et al. | 433/220 |
| 5,919,044 A | 7/1999 | Sicurelli, Jr. et al. | 433/220 |
| 5,921,778 A * | 7/1999 | Karmaker et al. | 433/215 |

(Continued)

FOREIGN PATENT DOCUMENTS

| | | | |
|---|---|---|---|
| DE | 20 2010 008938 | | 2/2011 |
| DE | 202010008938 | * | 2/2011 |

(Continued)

OTHER PUBLICATIONS

"Introduction to composite materials"—F.C. Campbell—Structural composite materials—2010 ASM International.*

(Continued)

*Primary Examiner* — Wade Miles
*Assistant Examiner* — Matthew P Saunders
(74) *Attorney, Agent, or Firm* — Ostrolenk Faber LLP

(57) ABSTRACT

The invention relates to an abutment for connecting a dental prosthesis to a dental implant, the abutment including a body portion for supporting the dental prosthesis and a contact surface apical to the body portion for contacting the dental implant. In order to allow an adjustment of the tooth restoration structure to properties of a natural tooth the abutment is composed of a resin that is reinforced with fibers substantially extending over the total length of the body portion towards the contact surface.

20 Claims, 3 Drawing Sheets

(56) References Cited

U.S. PATENT DOCUMENTS

| | | | | |
|---|---|---|---|---|
| 5,954,505 | A | 9/1999 | Ford | 433/177 |
| 6,030,220 | A * | 2/2000 | Karmaker et al. | 433/215 |
| 6,083,004 | A * | 7/2000 | Misch et al. | 433/173 |
| 6,193,516 | B1 | 2/2001 | Story | 433/173 |
| 6,267,597 | B1 * | 7/2001 | Kim | 433/224 |
| 6,287,122 | B1 * | 9/2001 | Seeram et al. | 433/220 |
| 6,371,763 | B1 | 4/2002 | Sicurelli, Jr. et al. | 433/220 |
| 6,381,989 | B1 * | 5/2002 | Karmaker et al. | 65/384 |
| 6,402,519 | B1 * | 6/2002 | Nordin | A61C 13/30 433/220 |
| 7,235,290 | B2 * | 6/2007 | Vallittu et al. | 428/296.7 |
| 7,335,250 | B2 * | 2/2008 | Burtscher et al. | 106/35 |
| 7,673,550 | B2 * | 3/2010 | Karmaker et al. | 87/1 |
| 7,682,152 | B2 | 3/2010 | Ford et al. | 433/174 |
| 7,850,452 | B2 | 12/2010 | Suttin et al. | 433/174 |
| 7,887,327 | B2 * | 2/2011 | Marotta | 433/213 |
| 7,997,901 | B2 | 8/2011 | Karmaker | 433/224 |
| 2002/0025506 | A1 * | 2/2002 | Hagenbuch et al. | 433/201.1 |
| 2003/0057590 | A1 | 3/2003 | Loher et al. | 264/157 |
| 2004/0053194 | A1 * | 3/2004 | Carroll | A61C 8/005 433/172 |
| 2004/0234925 | A1 | 11/2004 | Benhamou | 433/173 |
| 2005/0266380 | A1 | 12/2005 | Soler et al. | 433/173 |
| 2005/0266382 | A1 | 12/2005 | Soler et al. | 433/173 |
| 2006/0208393 | A1 * | 9/2006 | Karmaker et al. | 264/230 |
| 2007/0141532 | A1 | 6/2007 | Ford et al. | 433/173 |
| 2007/0141535 | A1 | 6/2007 | Baldissara | 433/173 |
| 2008/0020343 | A1 * | 1/2008 | Mount | 433/172 |
| 2008/0124682 | A1 | 5/2008 | Nordin et al. | 433/220 |
| 2008/0261176 | A1 * | 10/2008 | Hurson | 433/174 |
| 2009/0061385 | A1 | 3/2009 | Bahcall et al. | 433/173 |
| 2009/0061389 | A1 * | 3/2009 | Lomicka et al. | 433/201.1 |
| 2009/0092950 | A1 | 4/2009 | Machado | 433/225 |
| 2009/0123888 | A1 * | 5/2009 | Rosenberg | 433/173 |
| 2009/0123891 | A1 * | 5/2009 | Rosenberg | 433/174 |
| 2009/0176192 | A1 * | 7/2009 | Vallittu et al. | 433/215 |
| 2009/0258965 | A1 * | 10/2009 | Lassila et al. | 523/116 |
| 2010/0119994 | A1 * | 5/2010 | Feith | A61C 8/005 433/173 |
| 2010/0151420 | A1 | 6/2010 | Ranck | |
| 2010/0209877 | A1 * | 8/2010 | Hogan et al. | 433/214 |
| 2010/0304334 | A1 * | 12/2010 | Layton | A61C 8/005 433/173 |
| 2011/0033828 | A1 | 2/2011 | Nordin et al. | 433/221 |
| 2011/0250568 | A1 | 10/2011 | Machado | 433/225 |
| 2012/0107773 | A1 | 5/2012 | Lu et al. | 433/173 |
| 2012/0288824 | A1 | 11/2012 | Nordin et al. | 433/173 |
| 2014/0162215 | A1 * | 6/2014 | Feith | A61C 8/005 433/174 |

FOREIGN PATENT DOCUMENTS

| | | | | |
|---|---|---|---|---|
| EP | 1147748 | A2 * | 10/2001 | A61C 13/30 |
| EP | 1 319 375 | A1 | 6/2003 | |
| EP | 1319375 | A1 * | 6/2003 | |

OTHER PUBLICATIONS

European Search Report dated Oct. 19, 2011 issued in connection with corresponding European patent application No. EP 11 16 5565.
European Search Report dated Oct. 19, 2011 in related European Patent Application No. EP 11165560.1.

* cited by examiner

ABUTMENT FOR A DENTAL IMPLANT

FIELD OF THE INVENTION

The invention relates to an abutment for connecting a dental prosthesis to a dental implant, the abutment comprising a body portion for supporting the dental prosthesis and a contact surface apical to said body portion for contacting the dental implant.

BACKGROUND OF THE INVENTION

Prosthodontic restorations replacing a natural tooth in a patient's dentition are commonly fixed on a dental implant that is surgically implanted into the patient's jawbone. Typically, since the early work of Per-Ingvar Brånemark of Sweden in 1952, such an implant consists of a titanium screw which resembles a tooth root and comprises a roughened or smooth surface. The majority of dental implants are made out of pure titanium, which is commercially available in four grades depending upon the amount of contained carbon and iron.

An abutment is usually anchored at the coronal end of the dental implant. A dental prosthesis, such as a crown, a fixed bridge retainer or a removable denture, can be attached on the abutment serving as an interface between the dental prosthesis and the dental implant. The abutment is typically held in place with a screw. Abutments can be custom-made in a dental laboratory or purchased as a prefabricated part from a dental implant supplier.

Current abutments are typically made of titanium, stainless steel, gold or ceramic. All these materials have the disadvantage of being too stiff and brittle in comparison to the natural dentine they are supposed to replace and mimic. In consequence, the masticatory stresses exerted on the artificial tooth structure cannot be adequately absorbed. This leads to a number of undesirable side effects including an unnatural feeling of pressure while chewing, increased bruxism, and an increased risk of breakage of the artificial tooth structure. Another disadvantage lies in the different refractive indices of these materials from the refractive indices of the enamel and dentine of a natural tooth, resulting in an unnatural and unaesthetic appearance of the replacement structure. Moreover, these materials are difficult to rework, in particular to cut or grind or trim. In consequence, they are usually fabricated in specific standardized shapes which complicates an individual adaption to the shape of crown or bridge restorations.

OBJECTS AND SUMMARY OF THE INVENTION

It is an object of the present invention to avoid at least one of the above mentioned disadvantages and to provide an improved abutment which allows an adjustment of the tooth restoration structure to properties of a natural tooth.

Accordingly, the invention suggests that the abutment is composed of a resin that is reinforced with fibers substantially extending over the total length of the body portion towards the contact surface with the dental implant. The proposed material composition of the abutment permits mimicking of the properties of natural dentine in a number of ways, in particular with respect to the modulus of elasticity and/or the refractive index of natural dentine. Such a material can also provide an excellent biocompatibilty of the abutment. Moreover, the shape and size of the abutment can be easily reworked, even after its application on a dental implant, since the proposed material can be trimmed or cut similarly to natural dentine.

Despite its smooth workability, a high flexural strength of the body portion can be achieved, in particular in the range of 1500 MPa or higher, due to the continous longitudinal arrangement of the fibers. Thus, the abutment can be highly resistant against fracture, bending or rupture and can provide a long durability.

Generally, a number of different materials of the fiber and/or resin constituents of the abutment are conceivable. For instance, the material of the resin may be selected from methyl metacrylate (MMA), urethane dimethacrylate (UDMA), bisgma, epoxy, peek optima, polyester, polyvinyl ester or a mixture thereof. The material of the fibers may be selected from glass, quartz, carbon, aramide, kevlar or a mixture thereof. Moreover, a wide range of different compositions of the fiber content with respect to the resin content of the abutment is conceivable. Advantageously, the individual properties of these materials and of their relative composition can be exploited to adapt the abutment with respect to the specific requirements of the respective dental structure to be replaced.

In order to reduce the risk of breakage of the abutment, said body portion preferably exhibits a modulus of elasticity of at least 10 GPa and at most 50 GPa. In this way, the elastic properties of natural dentine can be imitated.

Preferably, the longitudinal extension of the fibers within the resin is exploited in such a way, that an anisotropic modulus of elasticity is achieved within the body portion. Thus, the body portion preferably exhibits a modulus of elasticity that varies dependently on the direction of a force applied to the body portion with respect to the orientation of a longitudinal axis extending in the apical direction of the body portion. In this way, the inherent properties of the natural two-layer system between the enamel and the dentine can be further simulated.

More precisely, anisotropic behavior of the modulus of elasticity of natural enamel and dentine has been reported in various scientific studies. Such anisotropic behavior of at least one layer of a multilayered biological system is believed to contribute to a protection against breakage or rupture of the system. Advantageously, the abutment according to the invention can be used to mimic the anistropic elastic modulus of one layer of such a natural system.

Preferably, the modulus of elasticity is lower for a force applied perpendicularly to the longitudinal axis of the abutment than for a force applied parallel to its longitudinal axis. In this way, a homogeneous and therefore predictable behavior can be achieved over the whole length of the body portion of the abutment. Preferably, the fiber content is chosen in such a way, that a variation of the elastic modulus of at least 10 GPa, more preferably at least 30 GPa, is achieved. Furthermore, the fiber content is preferably chosen in such a way, that a variation of the elastic modulus of at most 100 GPa, more preferably at most 40 GPa, is achieved. More specifically, the modulus of elasticity preferably varies between a value of at most 40 GPa for a force applied perpendicularly to said longitudinal axis and a value of at least 30 GPa for a force applied parallel to said longitudinal axis.

Various possibilities of the arrangement of the fibers within the resin are conceivable. According to a first preferred configuration, at least part of said fibers are substantially uniformly directed parallel to a longitudinal axis of said body portion. According to a second preferred configuration, at least part of said fibers are arranged in the manner of a braided netting in a biaxial or multiaxial orientation. Such an arrangement of the fibers can further contribute to improve the flexural strength of the abutment. In particular, an arrangement of the fibers can be applied as described in patent application No. EP 1 078 608 A1, which is hereby incorporated by reference.

A highly preferred material composition of the abutment comprises a resin that is derived from at least one methacrylate monomer, in particular methyl methacrylate (MMA) and/or urethane dimethacrylate (UDMA). Besides a high biocompatibility, an excellent bonding interaction between the abutment and the prosthetic structure can be expected from this material selection due to a chemical composition that resembles currently used composite resin cements that are used for fixing prosthetic devices in dentistry.

To provide an abutment that optically resembles the properties of natural dentine, in particular to render the abutment aesthetically more pleasing, the fibers are preferably constituted by glass fibers. For instance, E glass, S glass and/or AR Glass fibers are conceivable for that purpose. To further cause the abutment to simulate the optical properties of natural dentine, mineral particles are preferably embedded in said resin, wherein the content by volume of said mineral particles is matched in such a way that the index of refraction of said body portion is between 1.3 and 1.8, more preferably between 1.4 and 1.6. Most preferably, an index of refraction between 1.50 and 1.55 is achieved by an appropriate composition of said resin, fibers and mineral particles to closely imitate the appearance of natural dentine.

In use, a basic prerequisite of the abutment is its radiopacity to allow a dentist to monitor the artificial tooth structure by X-ray analysis. In order to provide this property of the abutment, X-ray absorbing particles are preferably embedded in said resin, said X-ray absorbing particles being selected from a chemical compound comprising an element with an atomic number of at least 37, more preferably of at least 57. Advantageously, the X-ray absorbing particles may be provided in the form of mineral particles for matching the refractive index of said body portion, as described above. Preferably, particles selected from an ytterbium compound are employed for this purpose, in particular ytterbium fluoride and/or ytterbium oxide.

In order to achieve the above described properties with respect to the abutment simulating natural dentine, while still ensuring a high flexural strength of the abutment, a fraction of at least 40% in volume of the total content of said body portion is constituted by said fibers. More preferably, the fiber content represents at least 70% of the total volume, and most preferably, about 80% of the total volume. This material exceeds currently used abutment materials with respect to its fatigue properties under repeated stress, in particular by at least a factor of five. A further improvement of the flexural strength and the elastic properties of the abutment can be achieved by pretensing the fibers during the manufacturing process, in particular by a tension force of at least 100 N, more preferably at least 300 N. Such a tensioning of the fibers can be advantageously implemented during a fabrication process that is carried out by means of pultrusion.

In order to improve the bonding interaction between the fibers and the resin, the circumferential surface of the fibers is preferably covered with a coupling agent, in particular silane, for enhancing the adhesion of said fibers to the resin. On the one hand, such a treatment of the fibers contributes to increase the interlaminate shear strength (ISS) of the abutment. In this way, an ISS-value of at least 80 MPa, in particular about 90 MPa or higher, can be achieved, resulting in a further improvement of the fatigue properties under repeated stress. On the other hand, a delamination of the abutment can be effectively avoided, in particular during a reworking of the prefabricated abutment shape, for instance by grinding or cutting the surface of the body portion by means of diamond burs or discs. This advantageously allows adapting the shape of the abutment to specific local requirements, even after it is fixed on a dental implant that is anchored in a jawbone.

Preferably, the shape of the body portion is substantially symmetrical with respect to a longitudinal axis of the abutment. In particular a cylindrical, cylindro-conical, conical, spherical or hyperbolic shape or a combination thereof is conceivable. More preferably, the body portion has a substantially hyperbolic form. Such a hyperboloid may be geometricaly described in a x-y-z coordinate system by the general equation $x^2/a^2+y^2/b^2-z^2/c^2=1$, wherein a, b, c are predefined constant values. More preferably, a circular hyperboloid is used, wherein a substantially equals b in the above equation. Such a hyperbolic body portion has the advantage of strengthening the overall tooth structure, in particular of providing a reduced risk of breakage, combined with a better distribution of lateral forces that are transmitted from the prosthetic structure. Another advantage is provided in conjunction with the reworkability of the abutment by means of commonly used cutting tools, such as diamond burs and/or disks, since the hyperbolic form allows an easier adaption to a specific shape and reduces the tendency of fracture of the abutment during the cutting or grinding procedure.

In order to further improve the bonding interaction between the abutment and the prosthetic structure, mechanical retention structures are preferably applied at the surface of the body portion. According to a first preferred configuration, the mechanical retentions can be provided in a micrometer sized range by trimming the surface of the body portion with appropriate cutting burs or tools.

According to a second preferred configuration, the mechanical retentions can be provided by means of at least one retention groove that is provided at the circumferential surface of the body portion. Preferably, at least two longitudinal grooves are provided extending in the apical direction of the body portion, wherein the course of each groove extends over a different portion of the circumference of the body portion. In this way, an improved retention can be achieved, wherein the danger of a structural weakening of the abutment is minimised. More preferably, the groove extends over the whole length of the body portion in order to increase mechanical retention along its total length. Moreover, the groove preferably exhibits an inclined course with respect to the longitudinal axis of the body portion for allowing an improved retention, in particular a substantially helical form that is at least partially winding or wrapped around the body portion. The preferred width and/or depth of the grooves is at least 0.01 mm and at most 1 mm, wherein a range in between 0.1 mm and 0.5 mm is more preferred. Preferably, at most ten, more preferably at most five, retention grooves are provided in order to minimize a structural weakening of the body portion. Other preferred characteristics of such a retention groove are described in patent application No. EP 2 281 525 A2, which is hereby enclosed by reference.

According to a third preferred configuration, an improved retention of the dental prosthesis on the abutment is achieved by combining both types of retention structures.

Preferably, the contact surface is constituted by a substantially flat bottom surface at the apical end of the body portion. This allows an easy application and positioning of the abutment on the dental implant before its actual fixation. Various fixation methods of the abutment on the implant are conceivable, in particular cementing, screwing or clipping or a combination thereof. Fixation by screwing can be achieved by means of an inward thread or an outward thread in or on the abutment. A particularly advantageous fixation of the abutment on the implant can be achieved by a receiving bore being provided at the contact surface for receiving a connector portion of the dental implant. Alternatively, a connector portion can be provided at the contact surface configured for insertion into a receiving bore of the dental implant. In particular the cross section of the receiving bore may exhibit a circular, squared, triangular, hexagonal or octogonal shape. In this way, a cost efficient and yet easy applicable and reliable fixation can be realized.

According to a preferred implementation of the abutment, the optical properties of the fiber-reinforced resin structure are exploited for an advantageous light conduction through the body portion, which can be used to achieve a proper polymerization of a setting product, such as resin cement. Advantageously, the ordered arrangement of the fibers extending over the total length of the body portion can be exploited to allow a superior light conduction both through the resin and through the optical fibers. Preferably, the optical fibers are glass fibers, in particular to provide an optical resemblance to natural dentine. Preferably, the apical surface of the body portion is used as a light entering surface. In particular, a planar cutting or grinding of the fibers may be applied for achieving an effective coupling of light into the fibers. Preferably, a light conduction to the contact surface is exploited for cementing the abutment to the dental implant.

Various fabrication methods can be applied for producing the described abutment, in particular extrusion, injection molding, wetting or pultrusion. Preferably, a pultrusion process is employed in which the fibers are pulled through a resin bath containing the above described mineral particles. Before the pultrusion, the fibers are preferably treated with a coupling agent, in particular silane, for enhancing the adhesion of said fibers to the resin. During the pultrusion process, the fibers are preferably tensioned by applying a tensile force of at least 50 N, more preferably at least 100 N, to increase the flexural strength and the elastic properties of the abutment according to the above description. After the pultrusion process, the shaping of the abutment can be achieved by molding and/or turning and/or grinding. Preferably, a turning lathe is used for this purpose.

BRIEF DESCRIPTION OF THE DRAWINGS

The invention will be described in more detail in the following description of preferred exemplary embodiments with reference to the accompanying drawings. In the drawings.

DETAILED DESCRIPTION OF THE PREFERRED EMBODIMENTS

Figure 1:
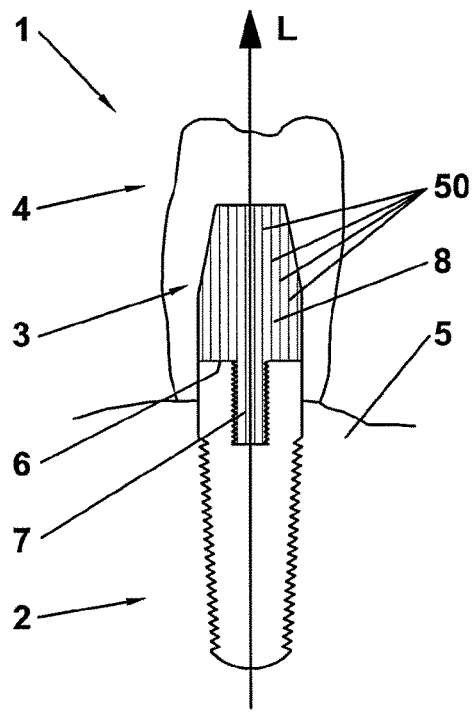
FIG. 1 is a schematic view of an artificial tooth structure according to a first embodiment in a longitudinal section.

FIG. 1 depicts an artificial tooth structure 1 comprising a dental implant 2, an abutment 3 and a dental prosthesis 4. The dental implant 2 is anchored into a jaw bone 5 and consists, for instance, of titanium, stainless steel, ceramics or another osseointegratable material.

The abutment 3 is arranged on the dental implant 2 in such a way that the abutment 3 has a contact surface 6 at its apical end with the coronal side of the implant 2. The abutment 3 is rigidly connected to the implant 2 by means of a connector portion 7 protruding from the center of the contact surface 6. The connector portion 7 is cylindrically shaped and has an outer thread that is engaged with an inner thread of a receiving bore in the implant 2.

The abutment 3 further comprises a body portion 8 which constitutes a prolongation of the implant 2 in a coronal direction along the longitudinal axis L. At the surface of the body portion 8 the dental prosthesis 4 is attached.

The abutment 3 is composed of a resin that is reinforced with fibers 50 extending over the total length of the body portion 8 to the contact surface 6. According to a first embodiment, the fibers are uniformly directed in parallel with respect to the longitudinal axis L of the body portion 8. According to a second embodiment, the fibers are arranged in the manner of a braided netting in a biaxial or multiaxial orientation. The resin consists of a polymer derived from a methacrylate monomer, preferably methyl methacrylate (MMA) or urethane dimethacrylate (UDMA). Mineral particles, preferably ytterbium fluoride and/or ytterbium oxide, are homogeneously distributed within the resin. The fibers are constituted by glass fibers, wherein the fiber content represents ideally 80% of the volume of the body portion 8. The fibers are treated with silane as a coupling agent to the resin matrix.

The abutment 3 exhibits several advantageous mechanical properties, in particular an elastic modulus similar to natural dentine that is anisotropic with respect to the longitudinal axis L and varying between 13 to 45 GPa. Yet the abutment 3 has a high flexural strength of about 1600 MPa for fracture resistance and durability. Moreover, the interlaminate shear strength (ISS) of the bond between the fibers and the resin matrix is larger than 90 Mpa, leading to improved fatigue properties under stress in comparison to competing materials such as titanium, stainless steel or ceramics. The shape of abutment 3 can be easily reworked by means of common cutting tools such as diamond burs and/or discs.

Furthermore, the abutment 3 has several advantageous optical properties. First, the incorporation of the mineral particles is chosen so that the material composition of glass fibers, resin and mineral particles yields an index of refraction of 1.52. This value corresponds closely to the refractive index of natural dentine (1.540). Secondly, the particular arrangement of the fibers in the resin allows good light conduction through the body portion 8. This can be exploited for a proper polymerization of a setting product, such as resin cement, in particular for fixing the abutment at its contact surface 6.

The mineral particles with a high atomic number embedded in the resin lead to a radiopacity of the body portion 8 that is larger than 200% of the radiopacity of Aluminium, more preferably above 400% of the radiopacity of Aluminium. The chemical composition of the resin material similar to composite resin cement permits a chemically profound bonding-interaction between the abutment 3 and the dental prosthesis 4 and/or the implant 2.

Figure 2:
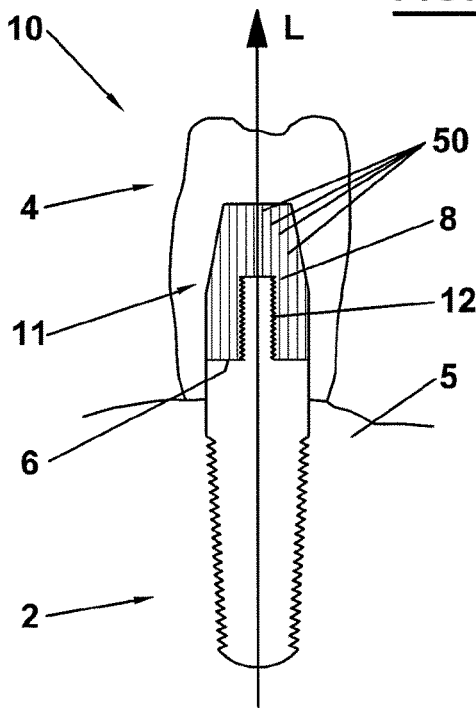
FIG. 2 is a schematic view of an artificial tooth structure according to a second embodiment in a longitudinal section.
Figure 3:
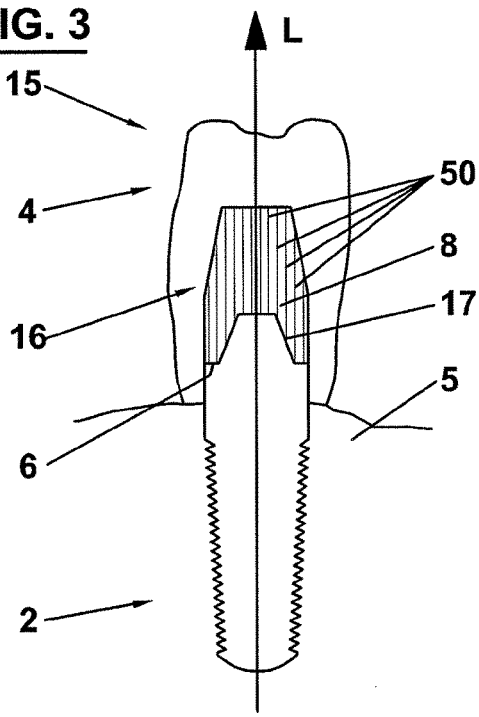
FIG. 3 is a schematic view of an artificial tooth structure according to a third embodiment in a longitudinal section.
Figure 4:
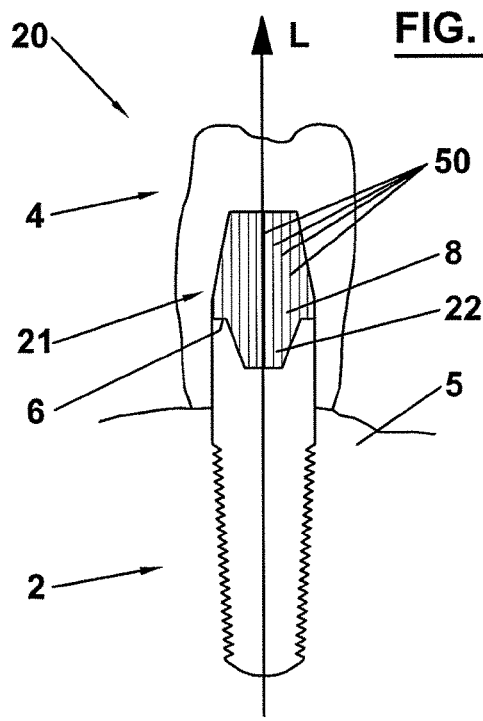
FIG. 4 is a schematic view of an artificial tooth structure according to a fourth embodiment in a longitudinal section.

The artificial tooth structures shown in FIGS. 2-4 comprise the dental implant 2, the dental prosthesis 4 and an abutment with essentially identical properties with respect to the material and shape of its body portion 8 as the abutment of FIG. 1. However, the connection means at the contact surface 6 of the abutment is modified from the connection means of FIG. 1.

FIG. 2 depicts an abutment 11 of an artificial tooth structure 10 that is rigidly connected to the implant 2 by means of a receiving bore 12 at the center of the contact surface 6. The receiving bore 12 is cylindrically shaped and has an inner thread that is engaged with a connector portion protruding from the coronal end of implant 2.

FIG. 3 depicts an abutment 16 of an artificial tooth structure 15 that is connected to the implant 2 by means of a receiving bore 17 at the center of the contact surface 6. The receiving bore 17 is octogonally shaped and receives an adequately shaped connector portion of the implant 2 in a form-fitted manner. A rigid connection between the abutment 16 and implant 2 at the contact surface 6 is established by means of resin cement.

FIG. 4 depicts an abutment 21 of an artificial tooth structure 20 that is connected to the implant 2 by means of a connector portion 22 protruding from the center of the contact surface 6. The connector portion 22 is octogonally shaped and is inserted in an adequately shaped receiving bore in the implant 2 in a form-fitted manner. A rigid connection between the abutment 21 and implant 2 at the contact surface 6 is established by means of resin cement.

In FIGS. 5-9 various abutments with a different shape of the body portion are depicted, which is symmetrical along the longitudinal axis of the abutment.

Figure 5:
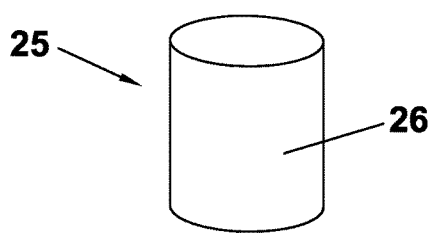
FIG. 5 is a schematic perspective view of the body portion of an abutment for a dental implant according to a first embodiment.

FIG. 5 shows an abutment 25 with a cylindrical shaped body portion 26.

Figure 6:
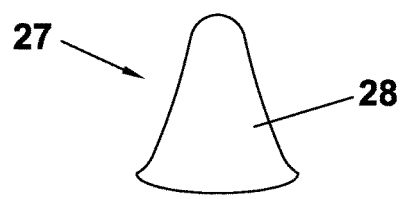
FIG. 6 is a schematic perspective view of the body portion of an abutment for a dental implant according to a second embodiment.

FIG. 6 shows an abutment 27 with a hyperboloidal body portion 28.

Figure 7:
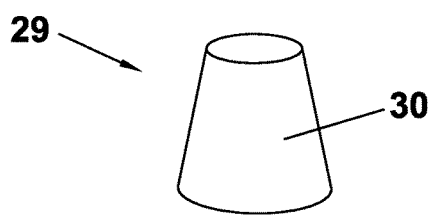
FIG. 7 is a schematic perspective view of the body portion of an abutment for a dental implant according to a third embodiment.

FIG. 7 shows an abutment 29 with a conical body portion 30.

Figure 8:
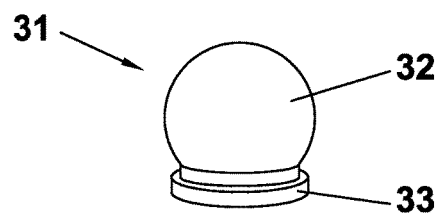
FIG. 8 is a schematic perspective view of the body portion of an abutment for a dental implant according to a fourth embodiment.

FIG. 8 shows an abutment 31 with a substantially spherical body portion 32. The body portion 32 comprises a cylindrical apical end 33 to be contacted with by the implant 2.

Figure 9:
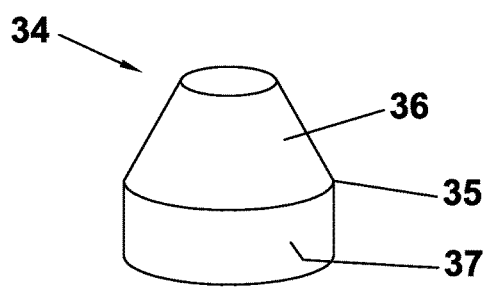
FIG. 9 is a schematic perspective view of the body portion of an abutment for a dental implant according to a fifth embodiment.

FIG. 9 shows an abutment 34 with a cono-cylindrically shaped body portion 35. The body portion 35 comprises a conical coronal part 36 and a cylindrical apical part 37.

Figure 10:
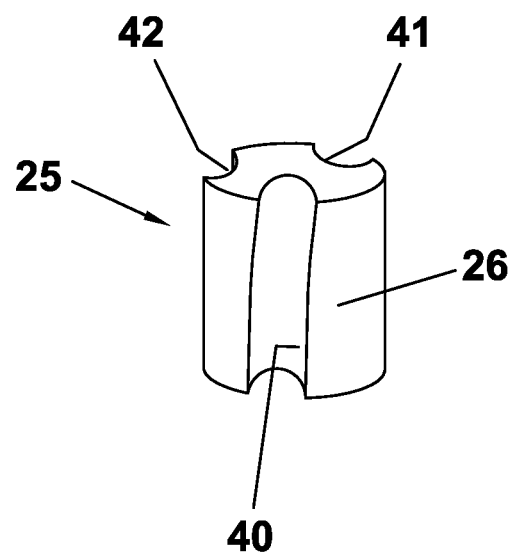
FIG. 10 is a schematic perspective view of the body portion of an abutment for a dental implant according to a sixth embodiment.
Figure 11:
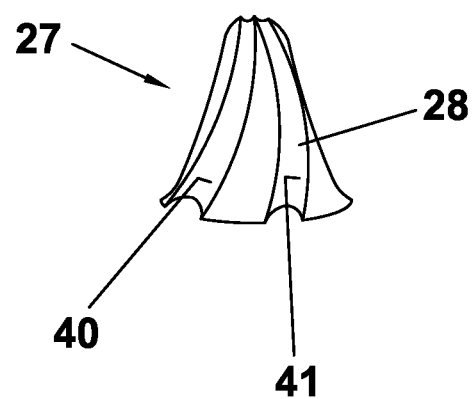
FIG. 11 is a schematic perspective view of the body portion of an abutment for a dental implant according to a seventh embodiment.

In FIGS. 10 and 11 an alternative embodiment of the abutments 25, 27 is depicted. Three retention grooves 40, 41, 42 are provided at the lateral surface of the body portion 26, 28. Each of the retention grooves 40, 41, 42 extends over a different circumferential portion of this surface in order to avoid a weakening of the structure and a risk of breakage. The course of retention grooves 40, 41, 42 substantially extends in the apical direction and over part of the circumference of the body portion 26, 28 such that they are partially wrapped around the surface. In this way, the retention properties can be greatly improved when the body portion 26, 28 is fixed in the dental prosthesis 4 by means of resin cement. Preferably, the grooves 40, 41, 42 extend over the total length of the body portion 26, 28 to increase mechanical retention along the total device length. The retention grooves 40, 41, 42 can be analogously applied on the body portion 30, 32, 35 of the abutments 29, 31, 34.

The above described preferred embodiments are intended to illustrate the principles of the invention, but not to limit the scope of the invention. Various other embodiments and modifications to those preferred embodiments may be made by those skilled in the art without departing from the scope of the present invention.

The invention claimed is:

1. An abutment for connecting a dental prosthesis to a dental implant configured to be anchored in a jawbone, the abutment comprising a body for supporting the dental prosthesis, a bottom contact surface at an apical end of said body for contacting the dental implant, and a top contact surface at a coronal end of said body for contacting the dental prosthesis, wherein the abutment is composed of a resin that is reinforced with fibers continuously extending over the total length of said body from said top contact surface towards said bottom contact surface, said body exhibits a modulus of elasticity varying dependent on a direction of a force applied to said body, said direction being defined with respect to an orientation of a longitudinal axis extending in an apical direction of said body, a receiving bore through said body with a center at a center of said bottom contact surface receives a connector of said implant or a connector of said abutment with a center at a center of said bottom contact surface protrudes from said bottom contact surface and is received in a receiving bore of said implant, a fraction of at least 40% in volume of the total content of said body is constituted by said fibers, said fibers are glass fibers, said resin is at least one polymer derived from at least one methacrylate monomer comprising at least one of urethane dimethacrylate and methyl methacrylate, mineral particles are embedded in said resin, the content by volume of said mineral particles being selected such that the index of refraction of said body is between 1.3 and 1.8, said mineral particles comprising X-ray absorbing particles, said X-ray absorbing particles being selected from a ytterbium compound, the abutment is configured to be anchored at a coronal end of the dental implant, such that the abutment, the dental implant, and the dental prosthesis form a prosthodontic restoration replacing a natural tooth, and at least two retention grooves are provided at a circumferential surface of said body, the retention grooves extending over the total length of said body in the apical direction of said body, the retention grooves having an inclined course with respect to said longitudinal axis such that the retention grooves comprise a helical form that is at least partially winding or wrapped around said body, the course of each groove extending over a different portion of the circumference of said body.

2. The abutment according to claim 1, wherein said body exhibits a modulus of elasticity of at least 10 GPa and at most 50 GPa.

3. The abutment according to claim 1, wherein at least part of said fibers are substantially uniformly directed parallel to said longitudinal axis.

4. The abutment according to claim 1, wherein at least part of said fibers are arranged in a manner of a braided netting in a biaxial or multiaxial orientation.

5. The abutment according to claim 1, wherein said mineral particles for setting the refractive index of said body are constituted by said X-ray absorbing particles.

6. The abutment according to claim 1, wherein a circumferential surface of said fibers is covered with a coupling agent for enhancing the adhesion of said fibers to said resin.

7. The abutment according to claim 1, wherein said body has a substantially hyperbolic form.

8. The abutment according to claim 1, wherein the content by volume of said mineral particles is selected such that the index of refraction of said body is between 1.4 and 1.6.

9. The abutment according to claim 1, wherein the content by volume of said mineral particles are selected such that the index of refraction of said body is between 1.50 and 1.55.

10. The abutment according to claim 1, wherein the content by volume of said mineral particles are selected such that the index of refraction of said body is 1.52.

11. The abutment according to claim 1, wherein all of said fibers continuously extend over the total length of said body towards said bottom contact surface, and a fraction of at least 70% in volume of the total content of said body is constituted by said fibers.

12. The abutment according to claim 1, wherein said mineral particles are selected from a ytterbium compound.

13. The abutment according to claim 1, wherein said fibers are optical fibers ending at said bottom contact surface at said apical end of said body such that light can be coupled into said fibers at said bottom contact surface.

14. The abutment according to claim 1, wherein a modulus of elasticity of said body is at least 30 GPa lower and at most 40 GPa lower for a force applied perpendicularly to said longitudinal axis than for a force applied parallel to said longitudinal axis.

15. The abutment according to claim 1, wherein said body of the abutment has a solid central portion, a central longitudinal axis of said body of the abutment extending in an apical direction of said body and through said solid central portion.

16. The abutment according to claim 1, wherein a central longitudinal axis of said body of the abutment extends through said receiving bore or said connector, and a length of said receiving bore is less than the total length of said body.

17. The abutment according to claim 1, wherein all of said fibers are substantially uniformly directed parallel to said longitudinal axis.

18. The abutment according to claim 1, wherein all of said fibers are arranged in a manner of a braided netting in a biaxial or multiaxial orientation.

19. The abutment according to claim 1, wherein a modulus of elasticity of said body varies between a value of at most 20 GPa for a force applied perpendicularly to said longitudinal axis and a value of at least 30 GPa for a force applied parallel to said longitudinal axis.

20. The abutment according to claim 1, wherein said bottom contact surface is flat and extends along a plane orthogonal to said longitudinal axis.

* * * * *